United States Patent [19]
Person et al.

[11] Patent Number: 5,490,856
[45] Date of Patent: Feb. 13, 1996

[54] PURSE STRING STAPLER

[75] Inventors: Wayne C. Person, Newtown, Conn.;
Marc J. Theroux, Slatersville, R.I.;
Kurt Azarbarzin, Brewster, N.Y.;
Richard N. Granger, Huntington, Conn.

[73] Assignee: Untied States Surgical Corporation, Norwalk, Conn.

[21] Appl. No.: 167,272

[22] Filed: Dec. 14, 1993

[51] Int. Cl.$^6$ ............................................. A61B 17/00
[52] U.S. Cl. ........................ 606/139; 606/148; 606/151; 227/175
[58] Field of Search .................... 606/139, 148, 606/144–146, 151, 142, 143; 227/175–178, 181, 19, 901

[56] References Cited

U.S. PATENT DOCUMENTS

| | | | |
|---|---|---|---|
| 2,457,379 | 12/1948 | Kallenbach | 606/146 |
| 3,665,926 | 5/1972 | Flores | 606/144 |
| 3,877,434 | 4/1975 | Ferguson et al. | |
| 4,345,600 | 8/1982 | Rothfuss | |
| 4,596,249 | 6/1986 | Freda et al. | 606/144 |
| 4,749,114 | 6/1988 | Green | |
| 4,773,420 | 9/1988 | Green | |
| 4,796,626 | 1/1989 | DeVries | |
| 4,821,939 | 4/1989 | Green | |
| 5,059,201 | 10/1991 | Asnis | |
| 5,152,769 | 10/1992 | Baber | 606/145 |
| 5,188,636 | 2/1993 | Fedotov | |
| 5,242,457 | 9/1993 | Akopov et al. | 606/144 |
| 5,246,156 | 9/1993 | Rothfuss et al. | 227/177 |

FOREIGN PATENT DOCUMENTS 1289475  2/1987  U.S.S.R. .................... 606/144

Primary Examiner—Stephen C. Pellegrino
Assistant Examiner—Jeffrey A. Schmidt

[57] ABSTRACT

An improved surgical stapler for applying a suture to a tissue is provided. The surgical stapler includes handles and a stapling assembly for emplacing a suture and staples into tissue as a purse string suture. Retainer structure, for example, a plurality of guides are provided for releasably retaining a portion of the suture substantially adjacent to the handles. The suture may also be releasably retained substantially adjacent to the handles by passing the suture through a tubular member releasably mounted on one of the handles. A clamp may be used to clamp and secure the suture within the tubular member either before or after removal of the tubular member from the handles.

22 Claims, 5 Drawing Sheets

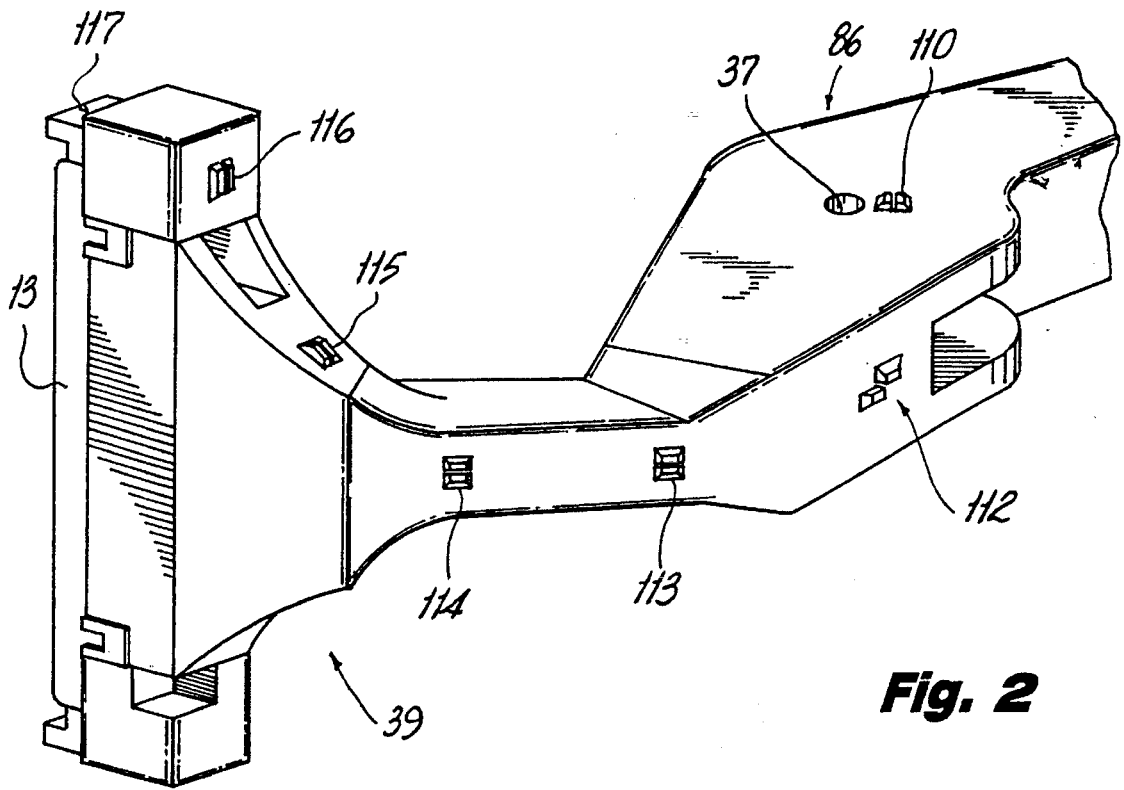
Fig. 2
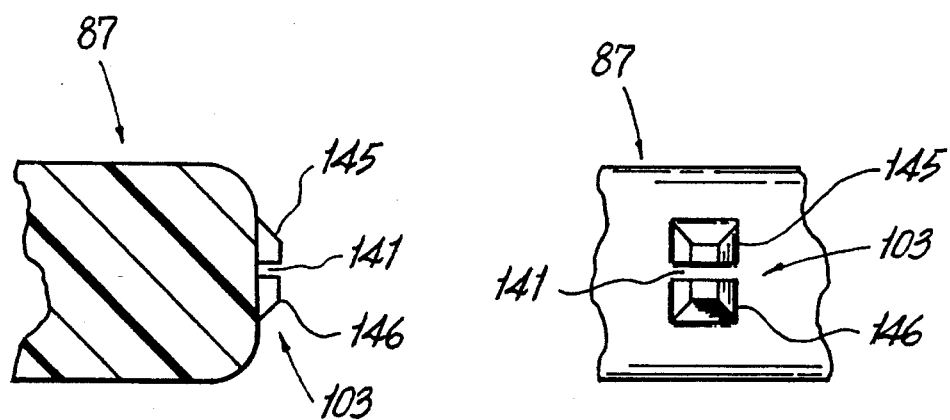
Fig. 3　　Fig. 4
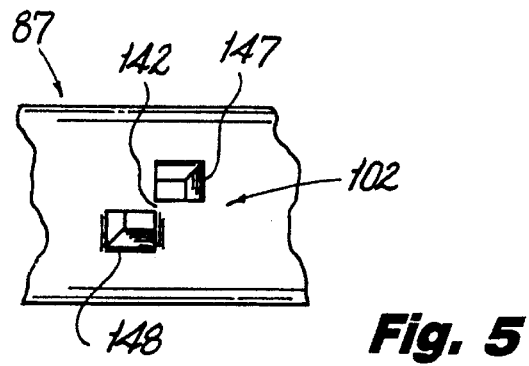
Fig. 5

5,490,856

PURSE STRING STAPLER

FIELD OF THE INVENTION

This invention relates to a surgical stapler and more particularly to a surgical stapler for affixing a purse string suture to tissue.

DESCRIPTION OF THE RELATED ART

Heretofore, it has been known to use purse string sutures and purse string appliers in the art of surgery. The suture is typically placed using a needle, staples or other suitable means for attaching the suture to the tissue. After attachment, the ends of the suture remain loose for pulling to contract or close the tissue. Conventional needles and instruments are well known in the art for inserting or attaching purse string sutures to tissue. For example, purse string surgical instruments utilizing needles and toothed jaws are disclosed in U.S. Pat. Nos. 4,345,600, 4,915,107 and 5,188,636. Commonly assigned U.S. Pat. Nos. 4,821,939 and 5,158,567 disclose purse string applicators with stapling cartridges for attaching a suture to tissue and are incorporated herein by reference.

Surgical instruments for attaching a purse string can require a relatively high degree of dexterity. Typically, for example, at least one free unattached end portion of the suture is in a loose state both during and after attachment to tissue. This requires the user of the surgical instrument to either hold or keep track of the unattached end portion. Furthermore, when attempting to pull the purse string to a desired tension, it can be difficult to maintain that tension while attempting other hand movements.

It would therefor be advantageous to provide a purse string instrument having means to hold or retain at least the end portion or portions of the suture during certain surgical procedures. This could further provide means to hold or retain the suture after the purse string is applied and/or while being pulled to a desired tension.

SUMMARY OF THE INVENTION

The present invention is primarily intended for use in cooperation with a surgical stapler for applying a suture to a tissue, with the surgical stapler including a handle, first retaining means for releasably retaining at least an end portion of the suture adjacent to the handle, and stapling means for applying staples to tissue and for attaching a suture to the tissue to form a purse string with the suture.

The present invention may further comprise second retaining means for releasably retaining at least a portion of the suture substantially adjacent the handle means. The second retaining means may include a plurality of guides having slots or other structure for releasably retaining a portion of the suture substantially adjacent the handle. Preferably, the first retaining means is a tubular member releasably mounted on the handle. The plurality of guides of the second retaining means can be integrally formed on the handle or be positioned on an exterior surface of the handle. The plurality of guides can be positioned along the handle and on means for mounting the stapling means to run a portion of the suture from the tubular member to the stapling means, including from one side to another side of the handle.

The present invention also comprises a method for using the surgical stapler having the suture releasably retained substantially adjacent thereto. The method comprises the steps of positioning the tissue adjacent the surgical stapler, applying a biasing force to the surgical stapler, emplacing at least one staple into the tissue to form the purse string with a portion of the suture, removing another portion of the suture from its position within retaining means on the surgical stapler, and tightening the suture about the tissue. In removing the suture from the surgical instrument, a user may first remove the entire retaining means, i.e., a tubular member retaining a portion of the suture. The step of tightening the suture may includes placing one end of the tubular retaining member adjacent the tissue and pulling the suture through the tubular member away from the tissue.

BRIEF DESCRIPTION OF THE DRAWINGS

The features of the present invention will become more readily apparent and may be better understood by referring to the following detailed description of an illustrative embodiment of the present invention, taken in conjunction with the accompanying drawings, where:

FIG. 2 shows an enlarged view of a distal end of the surgical stapler of FIG. 1;

FIG. 3 shows a side view of a suture guide;

FIG. 4 shows a top view of a first embodiment of the suture guide in FIG. 3;

FIG. 5 shows a top view of a second embodiment of the suture guide in FIG. 1;

DETAILED DESCRIPTION OF THE PREFERRED EMBODIMENTS

Figure 1:
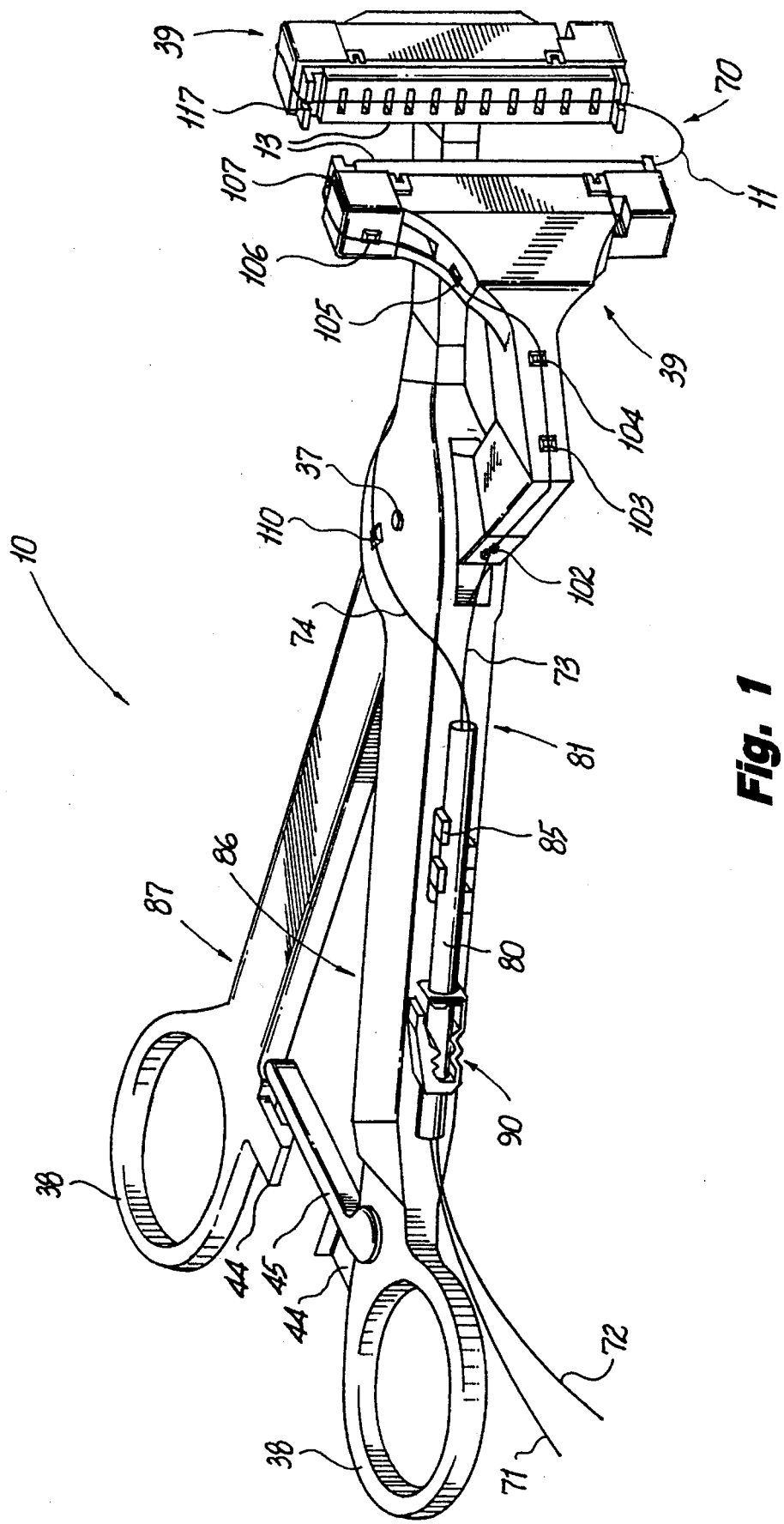
FIG. 1 shows a perspective view of a surgical stapler incorporating the present invention.

Referring now in specific detail to the drawings, with like reference numerals identifying similar or identical elements, the present invention is shown in cooperation with a surgical stapler for applying a suture to a tissue. As shown in FIG. 1, the surgical stapler 10 includes handles 86 and 87, a first retaining mechanism shown generally at 81 for releasably retaining a portion of suture 11 adjacent to handle 86, and stapling assembly 13 for emplacing staples into the tissue 12. Surgical stapler 10 in FIG. 1 is an anvilless surgical stapler and is substantially similar to that disclosed in commonly assigned U.S. Pat. No. 4,821,939 which is incorporated herein by reference.

Handles 86 and 87 of stapler 10 each have proximal and distal ends with stapling assemblies 13 disposed adjacent the distal ends and finger gripping portions 38 disposed at the proximal ends thereof. Handles 86 and 87 are pivotally connected to each other by pivot pin 37 as shown in FIG. 1. Resilient means such as a spring (not shown) may be included in stapler 10 to bias handles 86 and 87 apart in the absence of a biasing force from a user. Handles 86 and 87 are preferably fabricated from glass filled polycarbonate.

Stapler 10 further includes a catch mechanism 44 having a generally known construction disposed on the handles to hold the stapler 10 in a tissue clamping position after clamping of the handles. In addition, a safety mechanism 45 is provided at the proximal end of either handles 86 or 87 for preventing undesired clamping of the handles. Safety mechanism 45 is in the form of a lever pivotally mounted about a pivot such as a pin. Preferably, safety mechanism 45 is sized to permit pivoting by a thumb or a free finger of the user.

Figure 9:
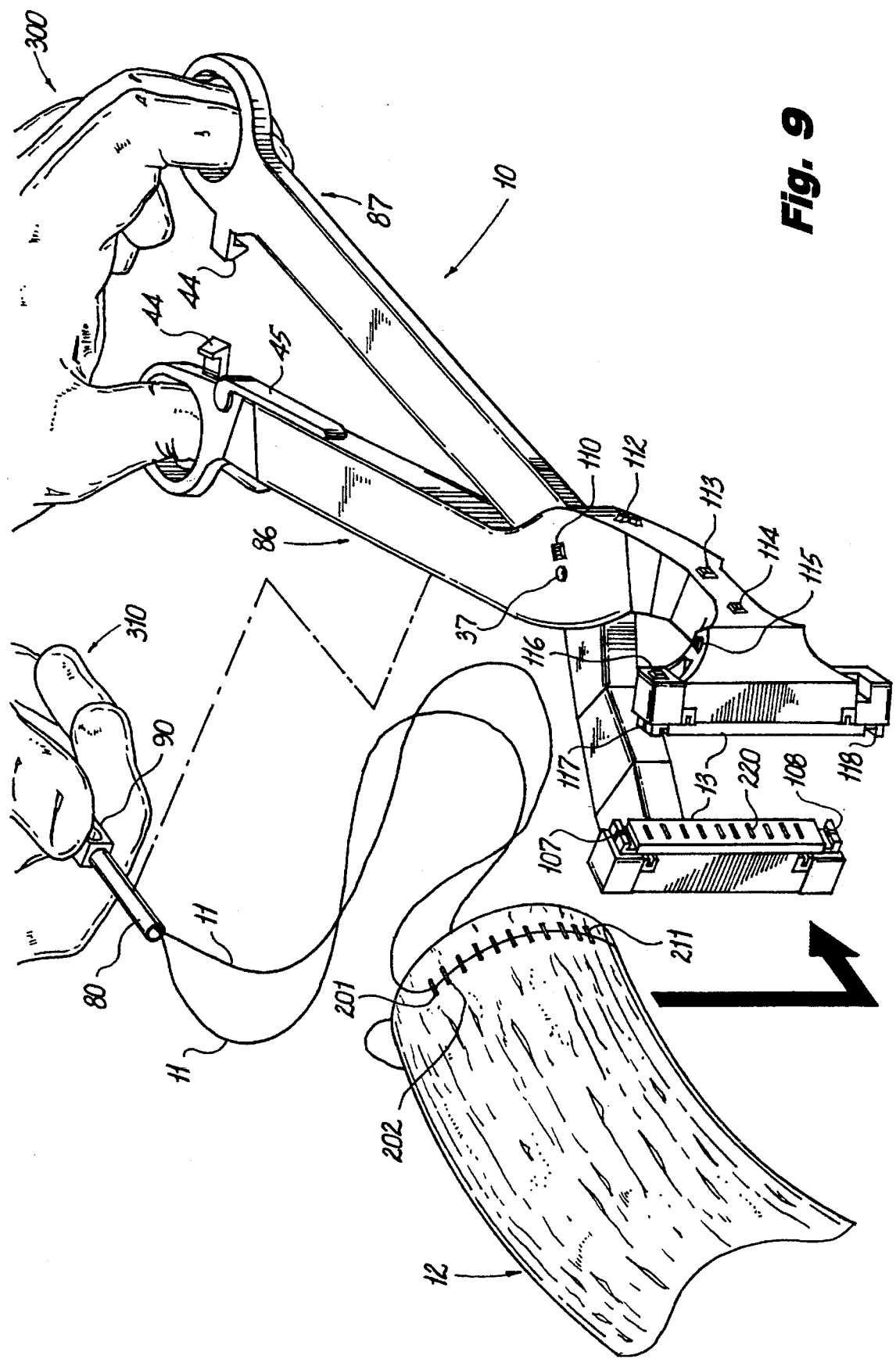
FIG. 9 illustrates the surgical stapler incorporating the present invention in use.

Turning to the suture of the instrument, with reference to FIGS. 1 and 9, suture 11 includes end portions 71, 72 and sections 73, 74 running from ends 71, 72. The suture runs along side handle 86 and through tubular member 80. A portion of the suture crosses to the distal end of handle 87 and the other end continues along handle 86 to the staple cartridge. Suture 11 is held in place and guided by a series of guides which will be discussed in greater detail below.

Figure 6:
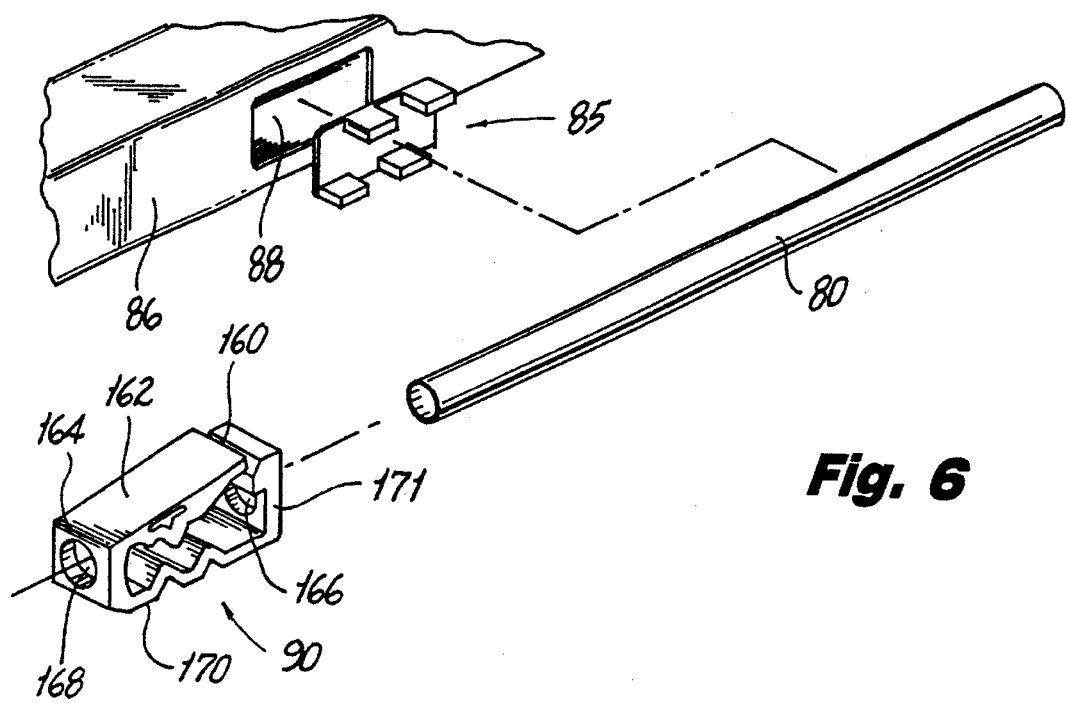
FIG. 6 illustrates an exploded view of structure for securing a suture.

A first retaining means 81 is releasably retained adjacent handle 86 (although, alternately, it can be positioned on handle 87) and includes a tubular member 80 through which a first portion of suture 11 is run. In a preferred embodiment, the tubular member 80 is an elongated tube of deformable plastic, such as 80 Duro polyvinyl chloride. The tubular member 80 releasably retains the suture 11 longitudinally along a length of the handle 86. Stapler 10 further includes mounting means for mounting the first retaining means to handle 86. With reference to FIGS. 1 and 6, tubular member 80 is mounted by holder 85 having a plurality of protrusions or teeth for releasably retaining tubular member 80 adjacent handle 86. Handle 86 includes a surface 88 forming a depression on an exterior surface thereof to allow holder 85 to be attached or mounted to a first side of the handle 86. Preferably, holder 85 is molded and integral with handle 86.

Figure 7:
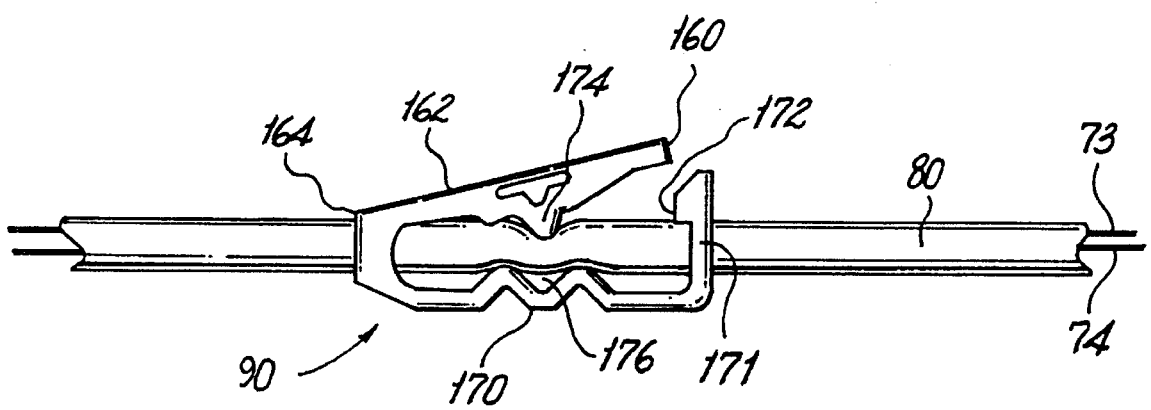
FIG. 7 illustrates a clamp of the securing structure in FIG. 6 in a first position.
Figure 8:
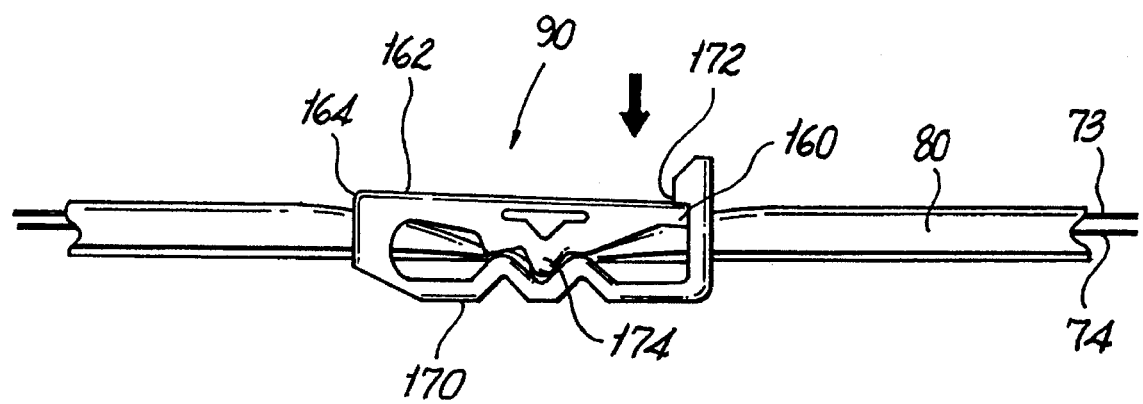
FIG. 8 illustrates the clamp of the securing means in FIG. 6 in a second position.

Retaining means 81 also includes clamp 90 for clamping and securing suture 11. As shown in FIGS. 6–8, clamp 90 is located adjacent the proximal end of the stapler 10 and positioned about tubular member 80 through which suture 11 is disposed. The proximal location of clamp 90 allows a user to grasp and engage the clamp during use of the stapler. With reference to FIG. 6, clamp 90 has a first edge 160, an upper surface 162, a lower surface 170 and hinge 164 connecting surfaces 162 and 170. Wall 171 protects upward from lower surface 170 and has a first opening 166 while hinge 164 has a second opening 168 to permit tubular member 80 to pass through clamp 90. Hinge 164 may be a living hinge, i.e., a hinge comprising a deformable material. Clamp 90, including hinge portion 164, may be made of a suitably flexible plastic such as LEXAN®.

As shown in FIG. 7, clamp 90 further includes edge 172 on wall 171, an upper protrusion 174 extending from the top surface 162, and a lower slot 176 formed from a curving of the lower surface 170. When clamped about tubular member 80, the unhinged end of top surface 162 catches under edge 172 and edge upper protrusion 174 abuts the exterior surface of tubular member 80 and pinches the tube into slot 176. This pinching serves to secure suture sections 73 and 74 in a fixed position with respect to tubular member 80.

In use, a user may hold the upper surface 162 and the lower surface 170 between a thumb and forefinger of one hand. Clamp 90 is locked in a closed position by applying pressure on upper and lower surfaces 162 and 170, respectively, causing upper surface 162 to pivot about hinge 164 until upper edge 160 locks under edge 172 (FIG. 8). By closing clamp 90, upper protrusion 174 compresses and deforms tubular member 80 as in FIG. 8 into lower slot 176, thereby holding tubular member 80 between upper protrusion 174 and the lower surface 170. With suture sections 73 and 74 disposed within tubular member 80, clamp 90 frictionally secures the suture sections within the tubular member. Referring to FIG. 9, with clamp 90 closed about tubular member 80 and suture 11 disposed therein, a user holds stapler 10 in a first hand 300 while second hand 310 removes releasably retained tubular member 80 from holder 85. In an alternative method of use, suture 11, may be removed from guides 102–106 and 110–116 (discussed below) by removing clamp 90 and tubular member 80 prior to the closing of clamp 90.

In a preferred embodiment, surgical stapler 10 further comprises second retaining means including a plurality of guides 102–106 and 110–116, as shown in FIGS. 1 and 9, for releasably retaining a portion of suture 11 substantially adjacent handles 86 and 87. The guides further provide means for running a portion of suture 11 from retaining means 81 to the stapling assemblies. In an alternative embodiment, a plurality of guides (such as described for the second retaining means) can be provided on handles 86 and 87 to releasably retain at least a portion of suture 11 substantially adjacent the handles, the guides being disposed from the proximal end to the distal end of the handles.

Turning to FIGS. 1–3, handle 87 has guides 102–106 and handle 86 has guides 110–116. As shown in a cross-sectional side view in FIG. 3, guides 102–106 and 110–116 comprises two elements 145 and 146 protruding from the exterior surface of the handles. Elements 145 and 146 define slot 141 therebetween, which is adapted for releasably retaining a portion of suture 11 by friction. Guides 102–106 and 110–116 may be separate components attached to handles 86 and 87, i.e., by adhesives or fusion, or can be integrally formed as part of the handles.

Guides 103–106, 110, and 113–116 are as shown in FIG. 4 with elements 145 and 146 symmetrical about a length of slot 141. The symmetry of guides 103–106, 110, and 113–116 about respective slots 141 allows the releasably retained portions of suture 11 to run in a substantially straight line through slots 141. Guide 110 serves as a cross-over guide for suture section 74 to be releasably retained from a first side of handle 86 to a second side and to an opposite third side of handle 86, where guides 112–116 releasably retain suture section 74. As shown in FIG. 1, suture section 73 crosses from handle 86 to handle 87 to be releasably retained substantially adjacent handle 87 by guides 102–106.

In a second embodiment of a suture guide, as shown in FIGS. 1 and 5, elements 147 and 148 are staggered or asymmetrical about a slot 142 formed therebetween. While elements 147 and 148 can be symmetrical about a center point in slot 142 approximately midway between the closest corners of the two elements 147 and 148, other equivalent embodiments of asymmetrical guide elements can also be employed. The asymmetry of the elements of guides 102 and 112 allow a portion of a suture 11 placed in slots 142 to be turned and/or bent at an angle and to be frictionally held by the sides and corners of elements 147 and 148. As shown in FIG. 1, staggered guide 102 releasably retains suture section 73 and permits the suture to bend when handles 86 and 87 pivot about pivot pin 37 during manipulation by a user. Suture section 74 is releasably retained by guide 110 to be run to the opposite, third side of handle 86, shown in FIG. 2, where staggered guide 112 releasably retains the suture section and provides means for turning the suture. Obviously, one skilled in the art would recognize that various combinations and equivalent embodiments of guides 102–106 and 110–116 may be employed to releasably retain suture 11 substantially adjacent the handles. The guides can further include a lip on each element over respective slots therebetween to facilitate retention of the suture in the respective slots.

Referring to FIGS. 1 and 9, suture 11 runs from ends 71 and 72, through tubular member 80, and through guides 102–106 and 110–116 to the stapling means, embodied as stapling assemblies 13. Second portion 70 of suture 11 is positioned substantially adjacent staples assemblies 13 disposed on the distal end of handle 87. Preferably, each stapling assembly 13 has third retaining means for releasably retaining suture portion 70 substantially adjacent each stapling assembly 13. The third retaining means includes guides 107, 108, 117 and 118, each having slots for releasably retaining the suture by friction.

During manufacture of the surgical stapler 10, suture 11 can be placed into guides 102–118 and through tubular member 80, with suture 11 strung taut between guides 102–118 to be disposed substantially adjacent handles 86 and 87 and stapling assemblies 13.

In use, with reference to FIG. 9, stapler 10 and tissue 12 are manipulated to dispose tissue 12 between stapling assemblies 13. Tissue 12 is typically a tubular organ such as an atrial appendage or bowel section. After proper positioning, the user pivots safety mechanism 45 away from handle 87 in order to permit firing of stapler 10. Upon firing, staples, i.e., 201–211, are ejected from recesses 220 in stapling assemblies 13. The staples are formed without use of an anvil and secure suture portion 70 to tissue 12, as disclosed in U.S. Pat. No. 4,821,939.

After firing stapler 10, a user having a free hand 310 can close clamp 90, as shown in FIG. 8, and remove the combination of clamp 90, tubular member 80, and suture 11 secured in tubular member 80 from holder 85 on stapler 10. Since suture 11 is releasably retained by guides 102–116, and, in an alternative embodiment by guides 107, 108, 117 and 118, suture 11, may then be removed from stapler 10. The user can then manipulate the clamp and suture to tighten or loosen the purse string about tissue 12. Preferably, with clamp 90 open, tubular member 80 is slid towards tissue 12 prior to pulling the purse string tight. This causes the pulling force to be substantially tangential to tissue 12. After tightening, clamp 90 can be closed to maintain the purse string by pinching tubular member 80 about suture 11. Alternatively, the user can also form the purse string, i.e., draw and tie tissue 12 in a secure purse string suture, and then cut the excess of suture 11 and remove tubular member 80, and clamp 90. Clamp 90 and tubular member 80 can be provided with readily recognizable shapes and colors to further aid visual identification during surgery.

Figure 10:
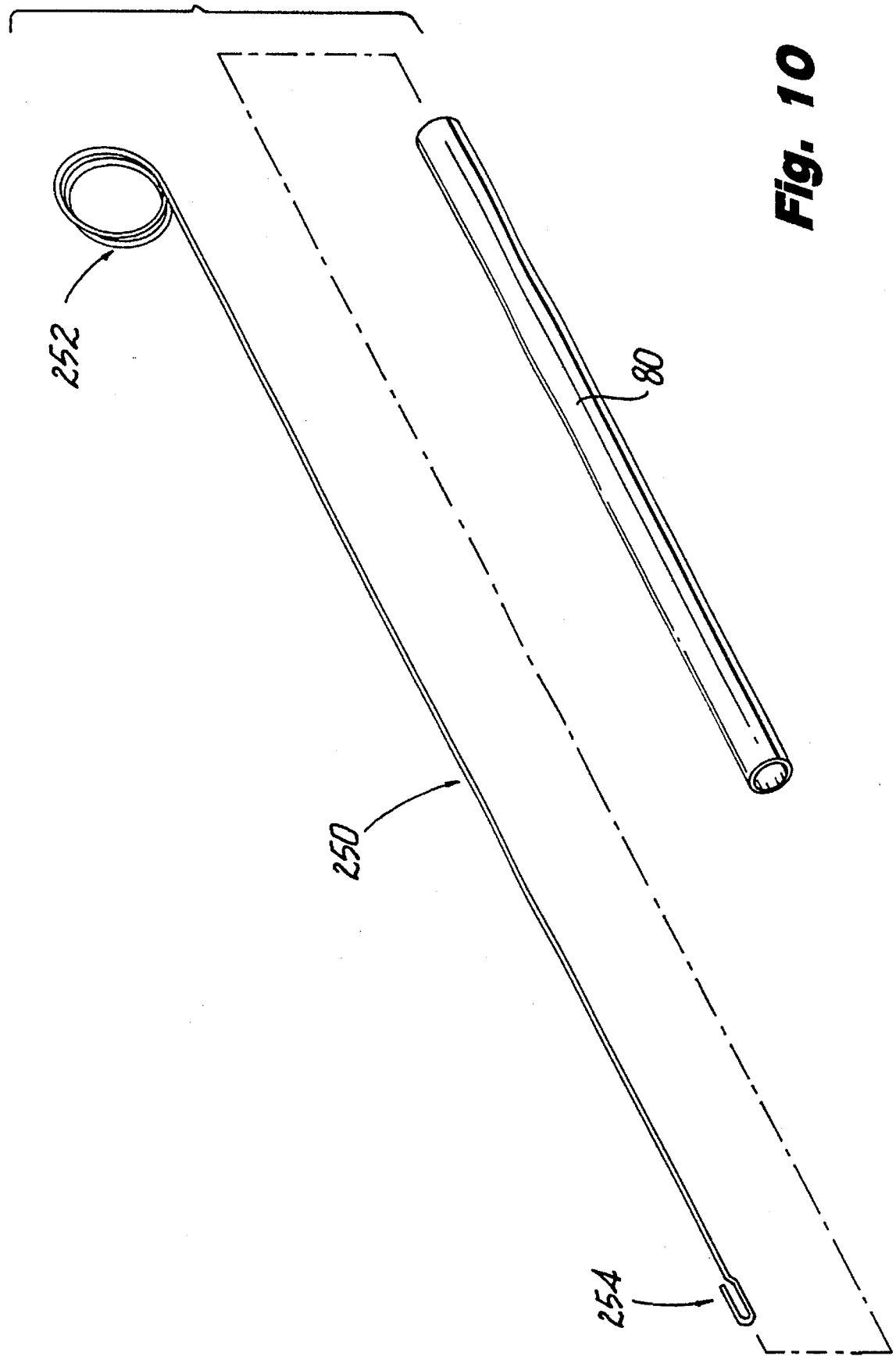
FIG. 10 illustrates a suture snare suitable for use with the present invention.

In the event tubular member 80 is moved relative to the suture while clamp 90 is not activated/closed, the suture may pull out of the tube. If this occurs, it may be advantageous to have a suture snare for retrieving the suture. With reference to FIG. 10, snare 250 has grasping portion 252 and hook portion 254. To retrieve a suture, snare 250 is simply passed through tubular member 80 and manipulated to catch the suture with hook portion 254. After the suture is properly hooked, snare 250 can be drawn out of tubular member 80 to enable the surgeon to grasp the suture and continue with the procedure. A suitable snare is disclosed, for example, in U.S. Pat. No. 4,796,626.

While the invention has been particularly shown and described with reference to the preferred embodiments, it will be understood by those skilled in the art that various modifications inform and detail may be made therein without departing from the scope and spirit of the invention. For example, while the present invention has been described in terms of first, second and third retaining means, such retaining means and their equivalents can be used alone or in any combination. Accordingly, modifications such as those suggested above, but not limited thereto, are to be considered within the scope of the invention.

What is claimed is:

1. A method for applying a purse string suture to tissue comprising:

providing a surgical stapler having a handle, stapling means and a suture having a portion thereof releasably retained substantially adjacent the handle by a tubular member, the method comprising the steps of:

positioning tissue to be stapled adjacent the stapling means;

applying a biasing force to the handle means;

securing at least one staple from the stapling means to tissue to form the purse string with at least a portion of the suture;

removing the tubular member and suture from the surgical stapler;

removing the surgical stapler from the tissue; and tightening the suture about the tissue.

2. The method as set forth in claim 1, wherein the step of tightening the suture comprises placing one end of said tubular member adjacent the tissue and pulling the suture through said tubular member away from the tissue.

3. The method as set forth in claim 1 further including the step of securing at least a portion of the suture within the tubular member using a clamp.

4. A suture retaining member for mounting a suture on an outer surface of a surgical instrument comprising:

a tubular member having a longitudinal bore extending therethrough;

a resiliently hinged clamp member cooperating with said tubular member for securing a suture at least partially disposed within the tubular member, the clamp member having a resiliently hinged portion for pivoting a first portion of the clamp member to compress the tubular member against a second portion of the clamp member and at least one opening formed within the resiliently hinged portion for passing the tubular member therethrough.

5. In a surgical stapler for applying a suture to tissue, the surgical stapler having at least one handle and means for applying a suture and staples to tissue, the improvement comprising:

a flexible tubular member removably mounted to said at least one handle, wherein the suture is at least partially disposed within the flexible tubular member.

6. The surgical stapler as set forth in claim 5, the improvement further comprising:

a plurality of guides disposed on said surgical stapler for releasably retaining at least a portion of a suture substantially adjacent the surgical stapler.

7. The surgical stapler as set forth in claim 5, wherein the stapler has first and second movable handles and the tubular member is removably mounted to the first movable handle.

8. A surgical stapler for applying a suture to tissue, the surgical stapler comprising:

a first handle having a distal end and a proximal end;

a suture at least partially disposed adjacent said first handle;

a tubular member disposed substantially adjacent said first handle, at least a portion of said suture being disposed within said tubular member;

a clamp associated with the tubular member, said clamp configured and dimensioned to compress said tubular member: and stapling means, disposed adjacent the distal end of said first handle, for applying at least one staple to tissue such that the suture, in combination with said at least one staple, forms a purse string with the tissue.

9. The surgical stapler as set forth in claim 8, further comprising a plurality of guides having slots for releasably retaining at least a portion of said suture substantially adjacent said first handle.

10. The surgical stapler as set forth in claim 9, wherein said plurality of guides are integrally formed on said first handle.

11. The surgical stapler as set forth in claim 9, wherein said plurality of guides are positioned on an exterior surface of said first handle.

12. The surgical stapler as set forth in claim 9, wherein:

said first handle includes means for mounting said stapling means adjacent the distal end of said handle; and at least one of said plurality of guides is positioned on an exterior surface of said mounting means.

13. The surgical stapler as set forth in claim 9, further comprising a second handle pivotally mounted to said first handle and at least one of said plurality of guides is positioned on an exterior surface of said second handle.

14. The surgical stapler as set forth in claim 13, wherein:

the exterior surface of the first handle includes a first side and a second side; and at least one of the plurality of guides is positioned on the first side for releasably retaining and guiding the suture from the first side to at least one guide positioned on the second side.

15. The surgical stapler as set forth in claim 9, wherein each of the plurality of guides includes:

two elements protruding from an exterior surface of said first handle to form one of said slots therebetween.

16. The surgical stapler as set forth in claim 15, wherein the two elements of at least one guide are symmetric about a length of the respective slot formed therebetween.

17. The surgical stapler as set forth in claim 15, wherein the two elements of at least one guide are asymmetric about a length of the respective slot formed therebetween.

18. The surgical stapler as set forth in claim 8, wherein said clamp has at least one opening for passing the tubular member therethrough and a hinge portion for pivoting a first portion of the clamp to compress the tubular member against a second portion of the clamp.

19. The surgical stapler as set forth in claim 8, further comprising a second handle and said tubular member is removably mounted on said first handle.

20. The surgical stapler as set forth in claim 19, further comprising a plurality of guides having slots positioned on an exterior surface of each said first and second handles for releasably retaining said suture substantially adjacent said first and second handles.

21. The surgical stapler as set forth in claim 8, wherein said stapling means are anvilless stapling means.

22. In a surgical stapler for applying a suture to tissue, the surgical stapler having at least one handle and means for applying a suture and staples to tissue, the improvement comprising:

a compressible tubular member removably mounted to the at least one handle; and a clamp disposed about a portion of the tubular member, the clamp being movable from a first position to a second position, wherein the tubular member is at least partially compressed by the clamp when the clamp is in the second position.

\* \* \* \* \*